(12) United States Patent
Ogihara et al.

(10) Patent No.: US 8,507,261 B2
(45) Date of Patent: Aug. 13, 2013

(54) INCUBATION CONTAINER

(75) Inventors: Yasushi Ogihara, Yokohama (JP); Ichiro Sase, Yokohama (JP); Roman Zantl, Baldham (DE)

(73) Assignee: Nikon Corporation, Tokyo (JP)

( * ) Notice: Subject to any disclaimer, the term of this patent is extended or adjusted under 35 U.S.C. 154(b) by 310 days.

(21) Appl. No.: 12/626,909

(22) Filed: Nov. 29, 2009

(65) Prior Publication Data

US 2010/0136671 A1    Jun. 3, 2010

Related U.S. Application Data (63) Continuation of application No. PCT/JP2008/060325, filed on May 29, 2008.

(30) Foreign Application Priority Data

May 30, 2007    (JP) .................................. 2007-142903

(51) Int. Cl.
  *C12M 1/34*    (2006.01)
  *C12M 3/00*    (2006.01)
(52) U.S. Cl.
  USPC .................. 435/288.4; 435/305.1; 435/305.2; 435/305.3; 435/287.1; 435/303.1
(58) Field of Classification Search
  USPC ............... 435/288.4, 305.1, 305.2, 305.3, 30, 435/34, 287.1, 288.7, 303.1
  See application file for complete search history.

(56) References Cited

U.S. PATENT DOCUMENTS

| | | | |
|---|---|---|---|
| 3,055,808 A | 9/1962 | Henderson | |
| 3,073,750 A | 1/1963 | Greenblatt | |
| 3,745,091 A * | 7/1973 | McCormick | ............... 435/305.3 |
| 3,902,972 A | 9/1975 | Beckford | |
| 3,983,993 A * | 10/1976 | Hsu | ................................ 206/1.7 |
| 4,668,663 A | 5/1987 | Boger | |
| 4,801,548 A * | 1/1989 | Takakura et al. | ........... 435/288.4 |
| D316,752 S * | 5/1991 | Ricketts | ....................... D24/226 |
| 2003/0189052 A1 * | 10/2003 | Greiner | ........................ 220/506 |
| 2004/0214313 A1 | 10/2004 | Zhang et al. | |

FOREIGN PATENT DOCUMENTS

| | | |
|---|---|---|
| JP | 56-053000 U | 10/1979 |
| JP | 62-001599 U | 1/1987 |
| JP | 63-137671 A | 6/1988 |

(Continued)

OTHER PUBLICATIONS

Office Action (Notice of Reasons for Rejection) issued on Mar. 26, 2013, in Japanese Patent Application No. 2009-549326.

*Primary Examiner* — Michael Marcheschi
*Assistant Examiner* — Shanta G Doe
(74) *Attorney, Agent, or Firm* — Miles & Stockbridge P.C.

(57) ABSTRACT

A laboratory dish comprises an incubation container, containing cultured cells, for observation through a microscope, in which a partitioning member partitions an interior of the incubation container into a plurality of incubation chambers by substantially perpendicular walls. The partitioning member tightly fits to a bottom portion of the incubation container, thereby capable of retaining in separation a liquid inputted in each of the incubation chambers from liquids in the other incubation chambers. A cover member covers an upper portion of each of the incubation chambers partitioned by the partitioning member and tightly fitted to the partitioning member. A whole or part of the cover member is formed of a transparent member, and the upper portion of each incubation chamber is formed with an opening via which to input the liquid.

14 Claims, 9 Drawing Sheets

(56) References Cited

FOREIGN PATENT DOCUMENTS

| | | |
|---|---|---|
| JP | 07-303470 A | 11/1995 |
| JP | 08-52366 A | 2/1996 |
| JP | 2000-166537 A | 6/2000 |
| JP | 2001-309777 A | 11/2001 |
| WO | WO 02/081314 A2 | 10/2002 |

* cited by examiner

|  | PARTITIONED-BY-2 PLASTIC | PARTITIONED-BY-4 PLASTIC | PARTITIONED-BY-2 GLASS BOTTOM | PARTITIONED-BY-4 GLASS BOTTOM |
|---|---|---|---|---|
| EXTERNAL CONTAINER | PLASTIC | | PLASTIC, GLASS IS BONDED TO BOTTOM PORTION | |
| PARTITION WALL | THREE PATTERNS ARE GIVEN BELOW;<br>• GLASS IS BONDED<br>• INTEGRAL MOLDING WITH EXTERNAL CONTAINER<br>• INTEGRAL MOLDING WITH INTERNAL COVER | | TWO PATTERNS ARE GIVEN BELOW;<br>• GLASS IS BONDED<br>• INTEGRAL MOLDING WITH INTERNAL COVER | |
| INTERNAL COVER | PLASTIC | | | |
| EXTERNAL COVER | PLASTIC | | | |

INCUBATION CONTAINER

CROSS-REFERENCE TO RELATED APPLICATION

This application is a continuation of International Application No. PCT/JP2008/060325 filed May 29, 2008.

TECHNICAL FIELD

The present invention relates to an incubation container that contains cultured cells.

BACKGROUND ART

Known as a conventional laboratory dish (Schale) is a partitioned laboratory dish defined as an incubation container disclosed in Japanese Patent Application Laid-Open No. 8-52366. The partitioned laboratory dish includes incubation chambers formed by partitioning an interior of a container of the laboratory dish with a for-the-use-of-Schale partitioning member that eliminates a necessity of pouring culture mediums separately into the partitioned incubation chambers.

To be specific, the partitioning member of the partitioned laboratory dish has a configuration that a whole or part of a partition base thereof does not tightly fit to a bottom surface of the laboratory dish, with the result that a plurality of sections (incubation chambers) in the interior of the partitioned laboratory dish communicate with each other at the bottom portion, and the culture medium, when poured into one section, spreads into all other sections within the same laboratory dish.

The partitioned laboratory dish is filled with a liquid containing a nutrient called a culture medium, and the cells are incubated on the bottom surface etc of the laboratory dish. The use of an inverted microscope enables observation of the cells on the bottom surface of the laboratory dish. A phase difference observation method enables a difference in refractive index between the cells to be converted into a contrast, whereby transparent cultured cells can be observed as they remain living.

The conventional laboratory dish exhibits such a phenomenon that when filled with the liquid defined as the culture medium, the liquid surface is not flat, and a liquid level in the vicinity of a wall surface of the partitioning member rises. The liquid level has a curvature, and hence a lens effect (this is called meniscus effect) occurs. Consequently, a phase difference illumination system gets lost its function, and a sufficient contrast is not acquired. None of problems arise in an area where the liquid surface existing sufficiently away from the wall surface is flat, however, there is a hindrance to the observation of the cells close to the wall surface of the partitioning member. Especially at the central portion of the partitioned laboratory dish, the partitioning member has a cross-shaped intersection, which hinders the observation.

Another problem of the conventional partitioned laboratory dish is that the partitioning member thereof has a gap at the bottom portion of the laboratory dish, and it is therefore impossible to observe a difference in reaction to the culture mediums between the cells by inputting the culture mediums under different conditions in the respective sections.

It is an object of the present invention, which was devised under such circumstances, to provide a laboratory dish capable of restraining the meniscus effect caused by the partitioning member of the partitioned laboratory dish and easily pouring and exchanging the liquid to be poured into the laboratory dish.

DISCLOSURE OF THE INVENTION

In order to solve the problems given above, a first aspect of the present invention is directed to an incubation container, containing cultured cells, for observation through a microscope, comprising: a partitioning member partitioning an interior of the incubation container into a plurality of incubation chambers by substantially perpendicular walls and tightly fitting to a bottom portion of the incubation container, thereby capable of retaining in separation a liquid inputted in each of the incubation chambers from liquids in the other incubation chambers; and a cover member covering an upper portion of each of the incubation chambers partitioned by the partitioning member and tightly fitted to the partitioning member, wherein a whole or part of the cover member is formed of a transparent member, and the upper portion of each of the incubation chambers is formed with an opening via which to input the liquid in each of the incubation chambers.

It is preferable that, in the incubation container according to the first aspect of present invention, each of the walls of the partitioning member has water-tightness, and a contact portion between the cover member and the partitioning member has the water-tightness.

It is preferable that, in the incubation container according to the first aspect of present invention, the cover member has a substantially circular flat portion and a cylindrical edge portion at an outside diametrical portion thereof and is positioned, with the flat portion being directed downward, substantially concentrically with the incubation container in the interior of the incubation container, an outside diametrical portion of the cover member is formed smaller than an inside diametrical portion of the incubation container, the flat portion and the cylindrical edge portion of the cover member are brought into contact with the partitioning member, a contact portion therebetween has the water-tightness, the opening is formed between the inside diametrical portion of the incubation container and the outside diametrical portion of the cover member, and the liquid can be poured via the opening into the incubation chambers and can fill up between the flat portion of the cover member and the bottom portion of the incubation container.

It is preferable that the incubation container according to the first aspect of the present invention, further comprising a second doughnut-shaped attachable/detachable cover member covering the opening between the inside diametrical portion of the incubation container and the outside diametrical portion of the second cover member.

A second aspect of the present invention provides an incubation container, containing cultured cells, for observation through a microscope, comprising:

a container body having a containing portion therein for containing said cultured cells, the containing portion being formed at a bottom thereof with an aperture;

a first cover member that closes said aperture;

a partitioning member partitioning said containing portion into a plurality of incubation chambers by substantially perpendicular walls and tightly fitting to said first cover member, thereby capable of retaining in separation liquid inputted in one of said incubation chambers from liquid(s) in the other incubation chamber(s);

a second cover member covering the upper part of said incubation chambers partitioned by said partitioning member; and said container body, said partitioning member and said second cover member being formed integrally; and said second cover member being so sized that an area thereof projected on the bottom of said containing portion is smaller than that of said aperture.

It is preferable that, in the incubation container according to the second aspect of the present invention, said first cover member is bonded to an outer surface of the bottom of said main body and an lower end surface of said partitioning member.

It is preferable that, in the incubation container according to the second aspect of the present invention, said first cover member comprises a cover made from a glass.

It is preferable that, in the incubation container according to the second aspect of the present invention, said aperture and said second cover member are substantially circular, and satisfy the following condition:

$$D2<d1$$

where d1 is a diameter of said aperture; and
d2 is a diameter of the cover member.

It is preferable that, in the incubation container according to the second aspect of the present invention, a surface of a wall of said partitioning member subtends an angle that is less than a predetermined angle with respect to the center axis of said partitioning member.

It is preferable that, in the incubation container according to the second aspect of the present invention, said angle is so determined to satisfy the following conditional expression;

$$\theta < \Delta/(n \times 2)$$

where Δ is an angle converted from an allowance of a phase plate with respect to a phase ring-shaped stop; θ denotes an angle between the surface of each wall of the partitioning member and the center axis I thereof; and n is refractive index of the culture medium.

It is preferable that, in the incubation container according to the second aspect of the present invention, the surface of said partitioning member and the surface of said second cover member are so formed to be optically smooth.

It is preferable that the incubation container according to the second aspect of the present invention, further comprises a third cover member that covers removably an inner diameter of said container body.

It is preferable that, in the incubation container according to the second aspect of the present invention, said third cover member covers a space formed between an inner diameter portion of said container and an outer diameter portion of said second cover member.

It is preferable that, in the incubation container according to the second aspect of the present invention, the wall of said partitioning member and said first cover member are watertight.

According to the present invention, it is possible to provide a laboratory dish capable of restraining the meniscus effect caused by the partitioning member of the partitioned laboratory dish and easily pouring and exchanging the liquid to be poured into the laboratory dish.

MOST PREFERRED EMBODIMENTS FOR CARRYING OUT THE INVENTION

Embodiments of the present invention will hereinafter be described with reference to the drawings.

First Embodiment

FIGS. 1 through 6 are explanatory views showing a plastic laboratory dish (Schale) partitioned by 4 into four chambers.

Figure 1:
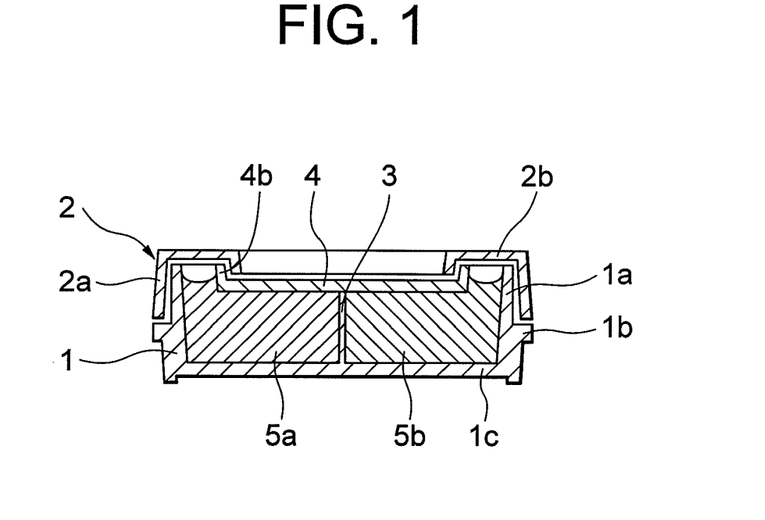
FIG. 1 is a sectional view of a laboratory dish according to a first embodiment of the present invention.
Figure 2:
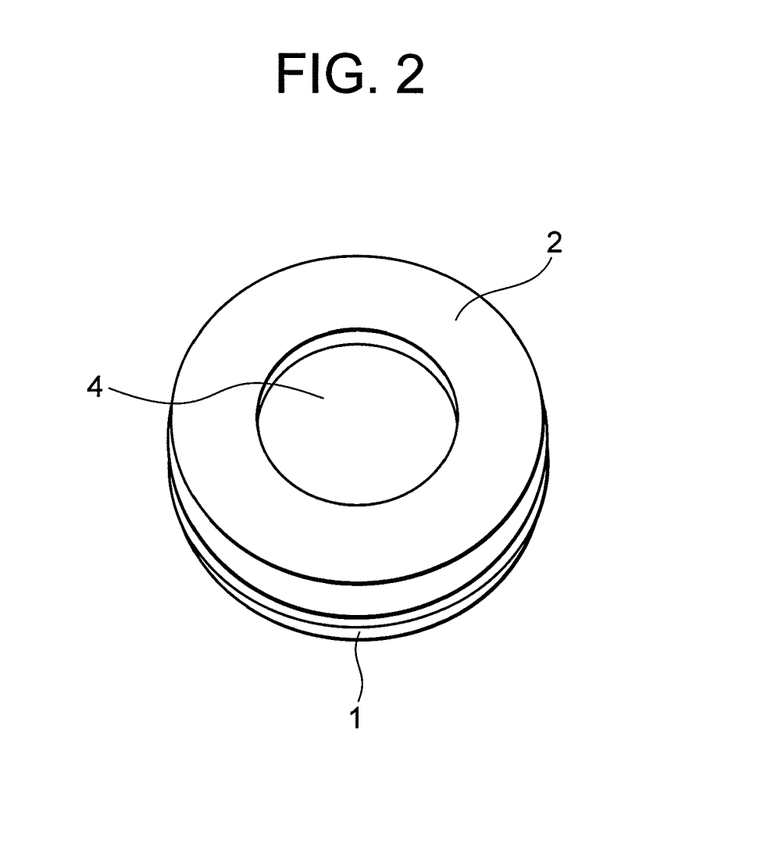
FIG. 2 is a perspective view of the laboratory dish.
Figure 3:
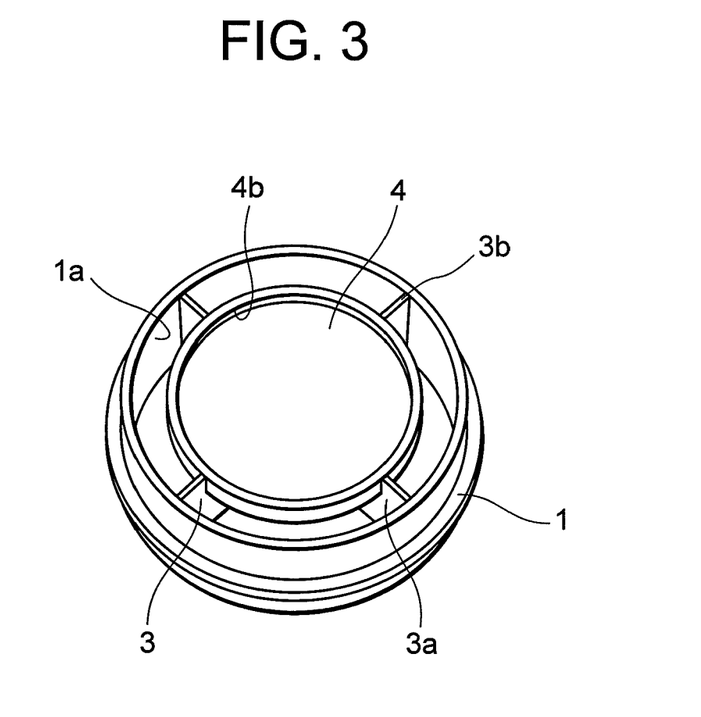
FIG. 3 is an explanatory perspective view that views an interior with an internal cover 4 with an external cover 2 of the laboratory dish being removed.
Figure 4:
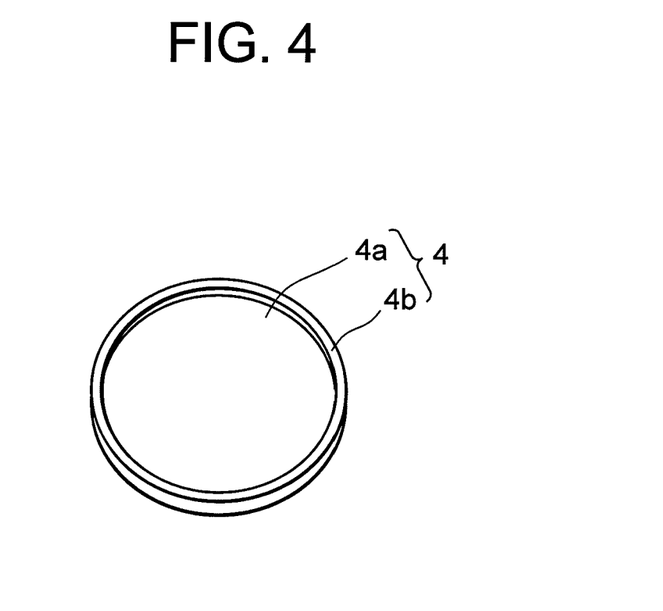
FIG. 4 is a perspective view of the internal cover 4 incorporated into the laboratory dish.
Figure 5:
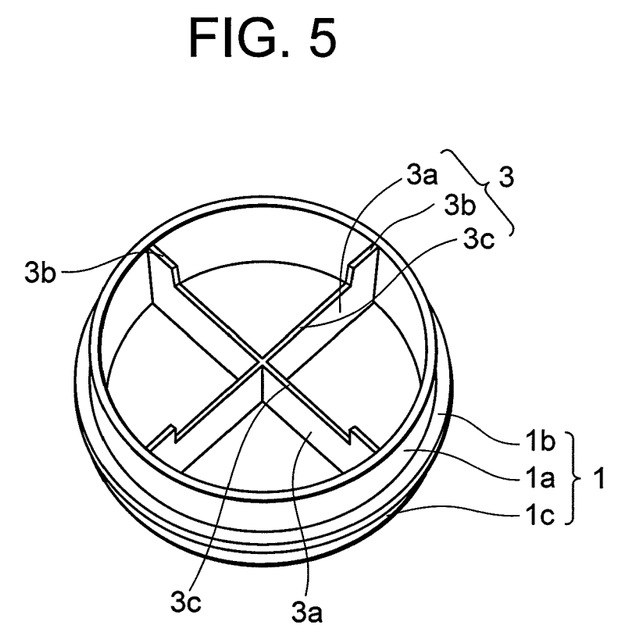
FIG. 5 is a perspective view that views the interior with none of the internal cover 4 with the external cover 2 of the laboratory dish being removed.
Figure 6:
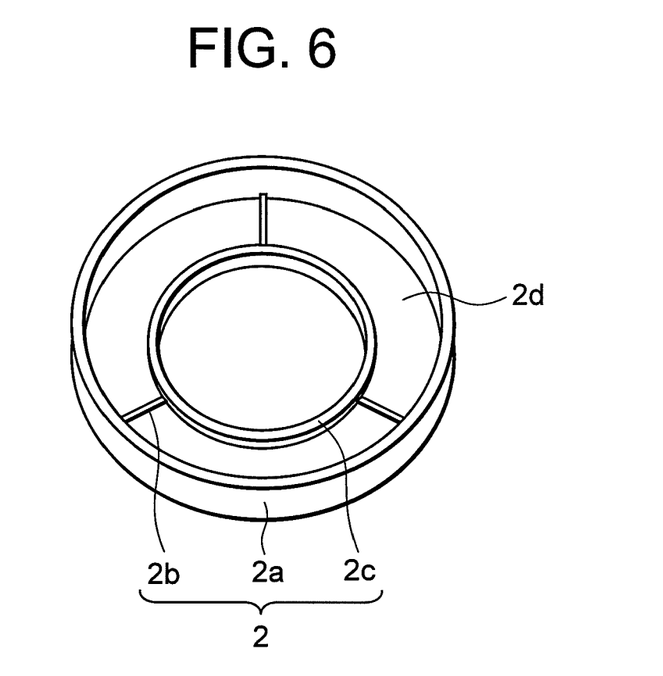
FIG. 6 is a perspective view of the external cover 2 as viewed from the backside.

FIG. 1 shows a sectional view of the laboratory dish. FIG. 2 is a perspective view of the laboratory dish. FIG. 3 shows a perspective view that views an interior of the laboratory dish with an internal cover 4 in a state that an external cover 2 is removed. FIG. 4 shows a perspective view of the internal cover 4 to be incorporated into the laboratory dish. FIG. 5 shows a perspective view that views the interior with none of the internal cover 4 in a state that the external cover 2 of the laboratory dish is removed. FIG. 6 shows a perspective view of the external cover 2 as viewed from the backside.

Referring to FIGS. 1 and 2, the laboratory dish is constructed of a laboratory dish body 1, a doughnut-shaped or ring-shaped external cover 2, a partitioning member 3 that partitions an interior of a container of the laboratory dish body 1 to form incubation chambers (sections), and the internal cover 4 tightly fitted to the partitioning member 3.

The laboratory dish body 1 is constructed of a cylindrical fitting portion 1a fitted in the external cover 2, an annular portion 1b protruding radially outside from the cylindrical fitting portion 1a, and a body portion 1c that forms a bottom portion.

Thus, the laboratory dish body 1 has the four incubation chambers partitioned by the substantially perpendicular walls 3a of the partitioning member 3 as completely independent spaces. The incubation chambers are respectively filled with different liquid culture mediums 5a, 5b, 5c (unillustrated), 5d (unillustrated). These culture mediums 5a, 5b, 5c, 5d, as illustrated in the drawings, entirely fill up the respective spaces between the bottom portion of the laboratory dish body 1 and the internal cover 4, thereby restraining a meniscus effect.

As illustrated in FIGS. 3-5, the laboratory dish has the partitioning member 3 that partitions the interior of the container of the laboratory dish body 1 into the four chambers. Each partitioning wall 3a of the partitioning member 3 has a radially outside portion 3b that is joined to the inner peripheral surface of the cylindrical fitting portion 1a of the laboratory dish body 1, and a central stepped portion 3c. Each radially outside portions 3b extends more upward than the stepped portions 3c of the partitioning member 3 and may abut on the protruded portions 2b of the external cover 2. An outer periphery of the upper end portion of the cylindrical end portion 1a and the inner periphery of the cylindrical edge portion of the outside cover 2 are fitted to each other. The upper end of the fitting portion 1a abuts on the protruded portions 2b of the external cover 2.

The internal cover 4 is fitted into the stepped portion 3c of the partitioning member 3, and the upper end face of the stepped portions 3c of the partitioning member 3 is bonded to the internal cover 4 by an adhesive agent.

The internal cover 4 is constructed of a circular flat portion 4a and a radially outside cylindrical edge portion 4b formed along the peripheral edge of the flat portion 4a. The internal cover 4 is so attached to the laboratory dish body 1 that the cylindrical edge portion 4b is fitted diametrically inside the radially outside portion 3b and the circular flat portion 4a is tightly mounted on the stepped portions 3c. The height of the upper end face of the cylindrical edge portion 4b is equal to or slightly lower than the height of the upper end face of the cylindrical fitting portion 1a.

Both of the partitioning member 3 and the internal cover 4 are formed of transparent members.

The partitioning member 3 and the internal cover 4 may take any configurations given below.

1) A first configuration is that the partitioning member 3 is bonded to within the container of the laboratory dish body 1, and the internal cover 4 is bonded to the partitioning member 3.

2) A second configuration is that the laboratory dish body 1 and the partitioning member 3 are integrally molded, and the internal cover 4 is bonded to the stepped portions 3c of the partitioning member 3.

3) A third configuration is that the partitioning member 3 and the internal cover 4 are integrally molded and then bonded to within the container of the laboratory dish body 1.

4) A fourth configuration is that the laboratory dish body 1, the partitioning member 3 and the internal cover 4 are integrally molded.

Referring to FIG. 6, the external cover 2 has effects in restraining evaporation of the culture mediums and in preventing contamination. Three pieces of minute protruded portions 2b abutting on the upper edge portions 3b of the partitioning member 3 are formed radially with a predetermined angular interval on the undersurface of a body portion 2d of the external cover 2, thereby ensuring minute gaps between the laboratory dish body 1 and the external cover 2 when the laboratory dish body 1 is covered with the external cover 2. The air is exchanged via these gaps, whereby the cells can be kept in a highly acceptable state.

An outer periphery of an innerside cylindrical portion 2c of the external cover 2 is formed in a way that fits to an inner periphery of an outer cylindrical portion 4b of the internal cover 4.

(Usage Method)

Next, a method of how the laboratory dish is used will be described.

Referring to FIG. 3, four liquids such as the culture mediums are poured into the incubation chambers via the doughnut-shaped gap between an inside diametrical portion of the fitting portion 1a of the laboratory dish body 1 and an outside diametrical portion of the outer cylindrical portion 4b of the internal cover 4.

Referring to FIG. 1, a liquid surface is opened at the doughnut-shaped gap between the inside diametrical portion of the fitting portion 1a of the laboratory dish body 1 and the outside diametrical portion of the outer cylindrical portion 4b of the internal cover 4, and therefore the liquid level has a curvature. At the central portion of the laboratory dish, however, the liquid surface is closed by the internal cover 4, and hence the liquid level becomes flat following the flat portion 4a of the internal cover 4. At the central portion of the laboratory dish, a phase difference observation can be made without any problem in the vicinity of the partitioning walls 3a of the partitioning member 3.

Second Embodiment

A second embodiment will hereinafter be described with reference to FIGS. 7 and 8 in a way that changes the reference numerals and symbols of the components different from those in the first embodiment, and omits the explanations of the same components.

Figure 7:
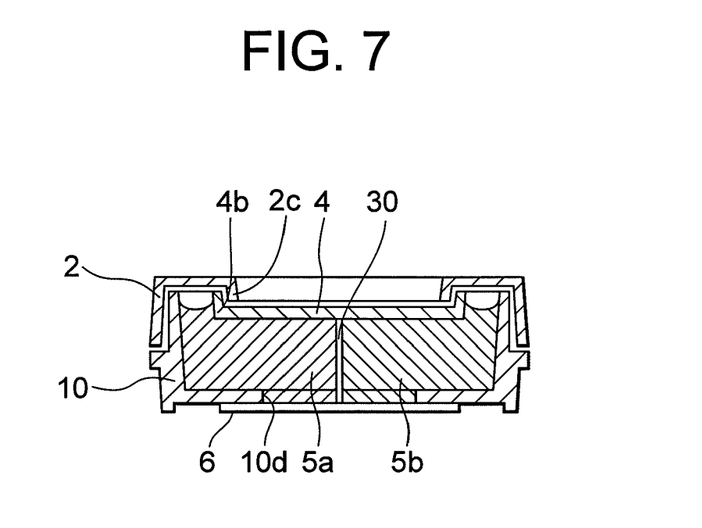
FIG. 7 is a sectional view of the laboratory dish according to a second embodiment of the present invention.
Figure 8:
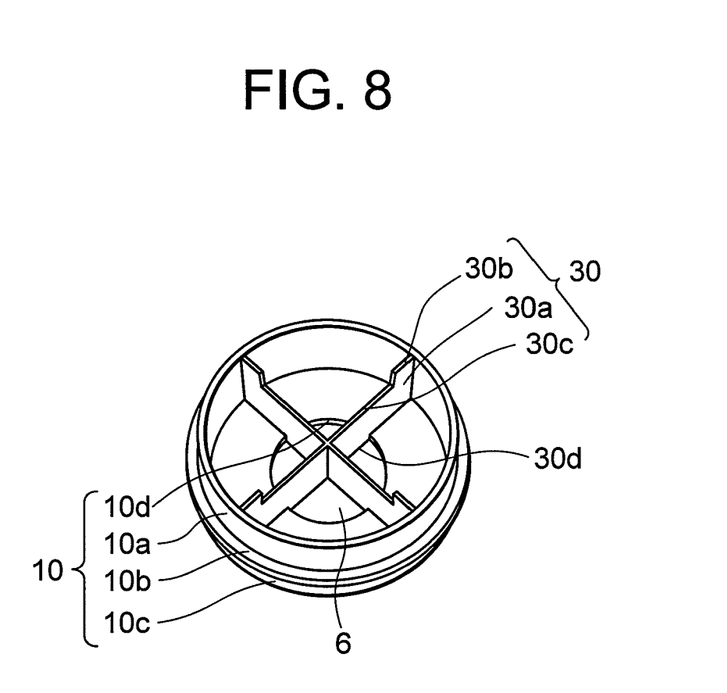
FIG. 8 is a perspective view that views the interior with none of the internal cover 4 with the external cover 2 of the laboratory dish being removed.

FIG. 7 illustrates the laboratory dish, in which the bottom of the laboratory dish body 1 is formed with a hole 10d and is bonded with a cover glass 6 from under as the container for observing the cells through a high-power objective lens having a short working distance. The laboratory dish, of which the laboratory dish body 10 is plastic-molded, is on the order of 1 mm in thickness. The cover glass 6 is as thin as 0.17 mm and therefore enables the high-power observation to be attained.

The laboratory dish has a partitioning member 30 that partitions the interior of the container of the laboratory dish body 10 into the four chambers. Each partitioning wall 30a of the partitioning member 30 has a radially outside portion 30b that is joined to the inner peripheral surface of the cylindrical fitting portion 10a of the laboratory dish body 10, and a central stepped portion 30c. Each radially outside portions 30b extends more upward than the stepped portions 30c of the partitioning member 30 and may abut on the radially extruded protruded portions 2b of the external cover 2. An outer periphery of the upper end portion of the cylindrical end portion 10a and the inner periphery of the cylindrical edge portion 2a of the outside cover 2 are fitted to each other. The upper end face of the fitting portion 10a abuts on the protruded portions 2b of the external cover 2. The lower end of each partitioning wall 30a of the partitioning member 30 is formed with a projection 30d to be tightly fitted in the bottom hole 10d of the laboratory dish body 1.

In order to form four completely independent chambers within the container of the laboratory dish body 10, the upper end of each steeped portion 30c of the partitioning member 30 is bonded to the internal cover 4 by an adhesive agent, and the projection 30d of the lower end of each partitioning wall 30a is bonded to the cover glass 6.

The same effects as those in the first embodiment can be acquired from this type of laboratory dish by taking the configuration of similarly applying the partitioning walls 30a of the partitioning member 30 and the internal cover 4.

Working Example

Figure 9:
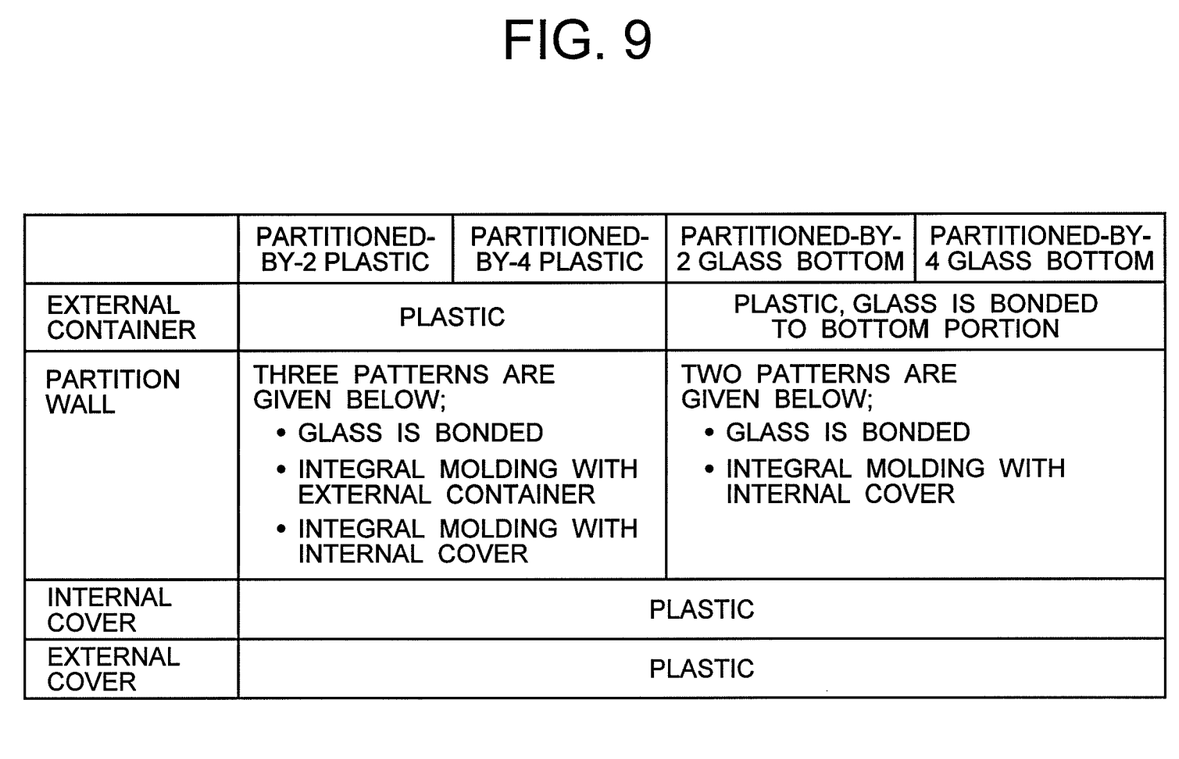
FIG. 9 is a diagram of a table showing types and materials of the laboratory dish.

The laboratory dishes illustrated in FIGS. 1 and 7 are constructed as shown in FIG. 9.

1) Purpose of the Laboratory Dish Partitioned by the Partitioning Member

Experiments using the plurality of culture mediums can be done simultaneously, and consequently the experimental efficiency rises.

Control data can be simultaneously obtained, and hence reliability of the data is improved.

2) Structure Etc of the Laboratory Dish

The basic material of the laboratory dish is the plastic.

The external container (the laboratory dish body 1, 10) is a normal type of dish taking the circular shape.

The partitioning walls (the partitioning walls of the partitioning member 3, 30) are configured by partitioning the dish by 2 or 4 into two or four chambers. The material thereof involves using the plastic or the glass.

The internal cover 4 serves to obviate the meniscus effect.

The external cover 2 servers to prevent contamination and the evaporation of the culture mediums.

Water-tightness:

Water-tightness is kept by bonding.

In the case of bonding the partitioning walls and the external container to each other, it is required that the water-tightness be ensured with a small quantity of bonding agent in order to secure the observable area that is as wide as possible.

Third Embodiment

Figure 10:
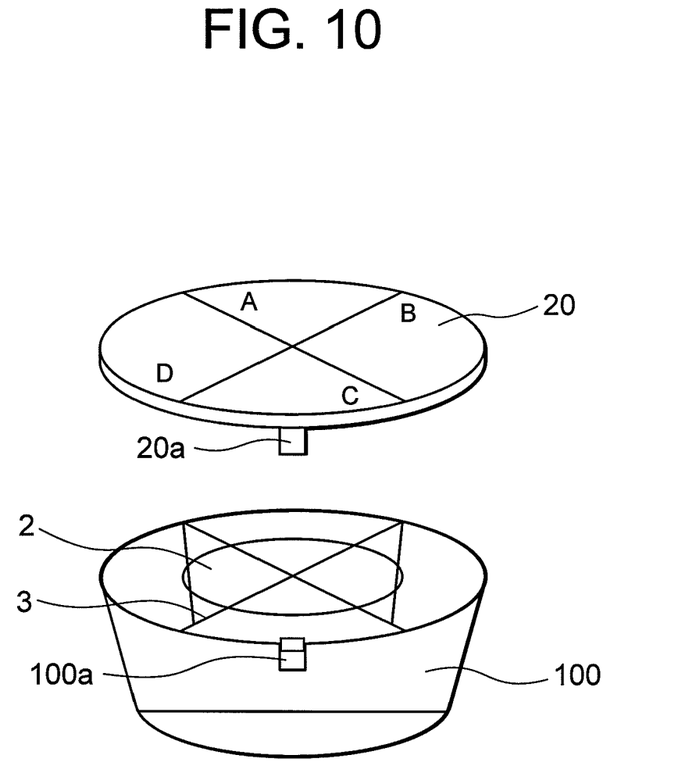
FIG. 10 is a view showing an external appearance of the laboratory dish according to a third embodiment of the present invention.
Figure 11:
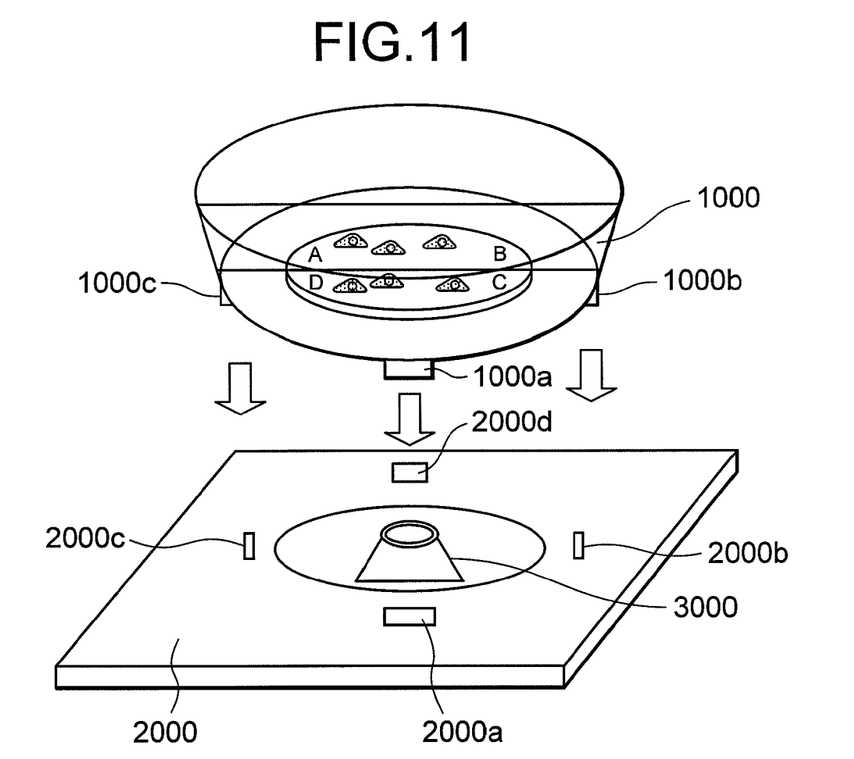
FIG. 11 is a view showing another laboratory dish according to the third embodiment of the present invention.

A third embodiment exemplifies the laboratory dish illustrated in FIGS. 10, 11 and is a partly-modified version of the laboratory dishes in the first and second embodiments. The laboratory dish in the third embodiment is simplified in illustration. Accordingly, the discussion on the third embodiment is focused on different portions from the first and second embodiments, and the explanations of the same portions are omitted.

The third embodiment has a contrivance for facilitating recognition of information specifying what types of cells are inputted in the partitioned incubation chambers of the laboratory dish, whether the culture mediums are inputted or not and what operation is applied to the cells.

In the laboratory dish in FIG. 10, an external cover 20 is formed with a protruded portion 20a, which is fitted in a recessed portion 100a formed in a laboratory dish body 100. With this configuration, a positional relationship between the external cover 20 and the laboratory dish body 100 is restricted, and positional relationships between the partitioned incubation chambers of the laboratory dish body 100 and marks A, B, C, D printed on the external cover 20 are determined.

The various items of information about the four incubation chambers of the laboratory dish body 100 can be recorded (in a storage device) in a way that associates these items of information with the marks A-D of the external cover 20.

Further, an example in FIG. 11 is that the bottom portion of a laboratory dish body 1000 is formed with protruded portions 1000a-1000d, which are respectively fitted into holes 2000a-2000d of a stage 2000 of a microscope, thus positioning the laboratory dish body 1000.

This configuration enables the microscope side to record the information specifying what kinds of cells and culture mediums are inputted in the four incubation chambers of the laboratory dish body 1000 and what operation is done.

Fourth Embodiment

FIGS. 12 to 16 are views for explaining a laboratory dish made of plastic and partitioned by 4 into four chambers according to a fourth embodiment of the present invention.

Figure 12:
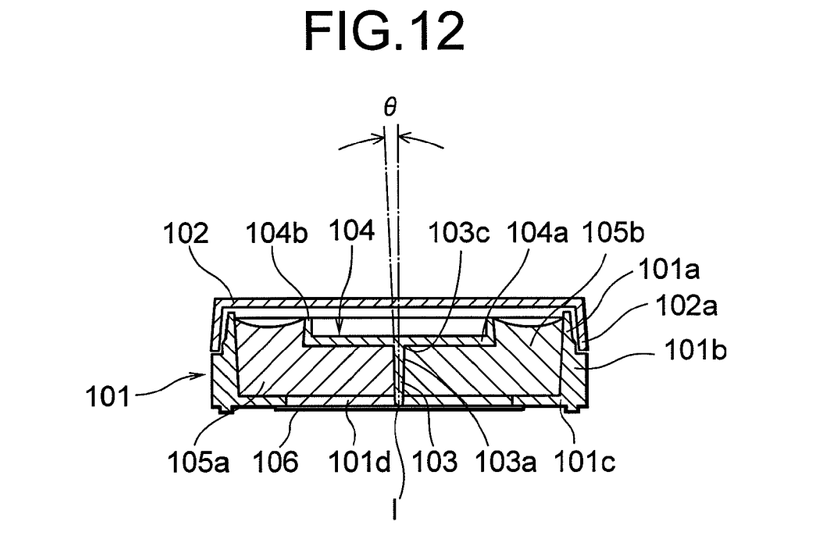
FIG. 12 is a view showing a cross section of a laboratory dish according to a fourth embodiment of the present invention with the outer cover being mounted.
Figure 13:
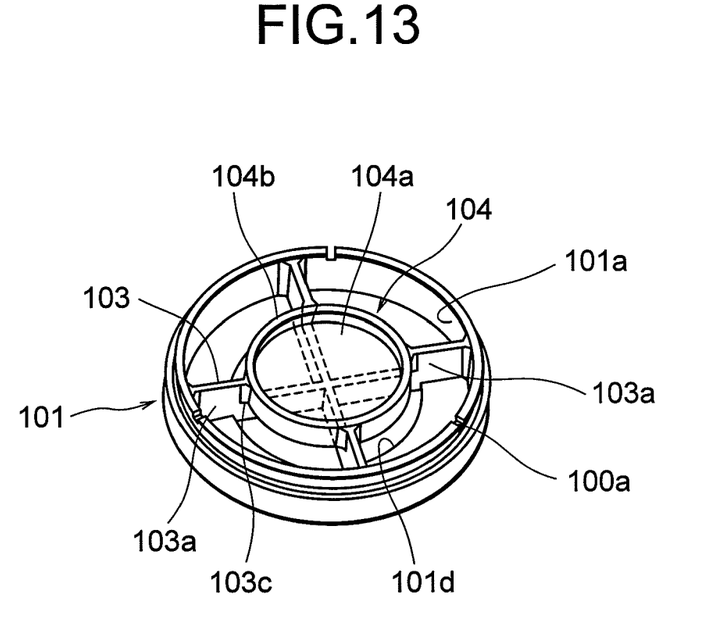
FIG. 13 is a perspective view of a main body of the laboratory dish according to the fourth embodiment with the external cover being removed.
Figure 14:
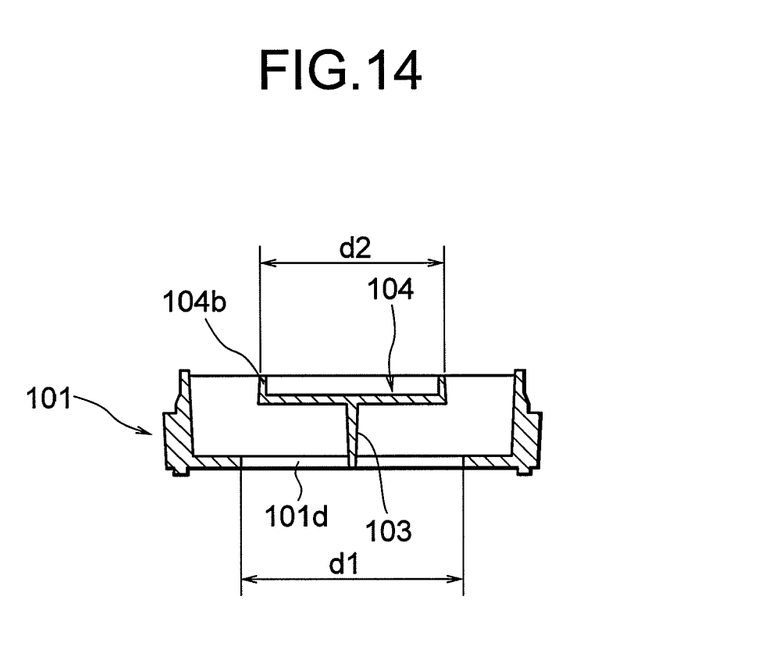
FIG. 14 is a sectional view of the main body of the laboratory dish showing a dimensional relationship between the internal cover and the aperture formed at the bottom of the body of the laboratory dish.

FIG. 12 is a sectional view of the laboratory dish with the external cover being attached. FIG. 13 is a perspective view of the laboratory dish body 101 with the external cover of the laboratory dish being removed. FIG. 14 is a cross sectional view showing dimensional relationship between the aperture 101d formed through the bottom of the laboratory dish body 101 and the internal cover 104.

Referring to FIGS. 12 and 13, the laboratory dish is composed of the laboratory dish body 101, the external cover 102 for closing the laboratory dish body 101, the partitioning member 103 for partitioning the insides of container of the laboratory dish body 101 into incubation chambers (sections), the internal cover 104 connected to the partitioning member 103. The external cover 102 may be doughnut-shaped or ring-shaped in the same way as in the first embodiment and may cover the space between the laboratory dish body 101 and the internal cover 104 that will be described hereinafter.

The laboratory dish body 101 is so structured integrally to have an outer cylindrical fitting portion 101a fitted in the radially outer cylindrical portion 102a of the external cover 102, an annular portion 101b radially outwardly projected from the cylindrical fitting portion 101a and a main body portion 101c formed with a bottom forming a central opening portion 101d.

To the laboratory dish body 101, the lower end face of the partitioning member 103 and the cover glass 106 are bonded with an adhesive so that four incubation chambers which are completely separated from each other, are formed by the partitioning member 103 as shown in FIG. 13. The four incubation chambers are filled with four different incubation liquids to form different culture medium, respectively. The culture medium 105a and 105b shown in FIG. 12 fill completely the respective chambers between the bottom portion of the laboratory dish body 101 and the internal cover 104, thereby the meniscus effect being restrained.

As shown in FIG. 13, the laboratory dish has the partitioning member 103 by which the inside of the container of the laboratory dish body 101 is partitioned by 4 into four chambers. The partitioning walls 103a each is integrally formed at an upper end 103c with the internal circular cover 104 whose outer diameter is smaller than the inner diameter of the aperture 101d formed at the bottom of the laboratory dish body 101.

The internal cover 104 is formed by a circular flat portion 104a and the cylindrical edge portion 104b projected upward at the peripheral edge of the flat portion 104a. The height of the upper end of the circular edge portion 104b is slightly lower than that of the upper end of the cylindrical fitting portion 101a.

The laboratory dish body 101c, the partitioning member 103 and the internal cover 104 are all made of transparent plastic and are integrally molded by a known injection molding process.

A cover glass 106 is bonded to the underside surface of the bottom of the partitioning member 103 and closes the aperture 101d at the bottom of the laboratory dish body 101c. The partitioning member 103 is protruded through the bottom aperture 101d of the laboratory dish body 101 and bonded to the cover glass 106, thereby four independent incubation chambers being formed.

The cover glass 106 provided to close the bottom aperture 101d of the laboratory dish body 101c enables cultured cells to be observed through the cover glass 106 with a high power objective lens.

As shown in FIG. 14, the laboratory dish body 101 is so structured that the condition $d_2<d_1$ is satisfied, where d1 denotes the diameter of the aperture 101d formed through the bottom of the laboratory body portion 101, and d2 denotes the diameter of the outer periphery 104b of the internal cover 104.

By satisfying the condition $d_2<d_1$, the molded laboratory dish body 101 may be easily removed out of the dies, when the laboratory dish body 101 is integrally formed by injection molding process. Thus, the laboratory dish body 101 may be produced less expensively.

Figure 15:
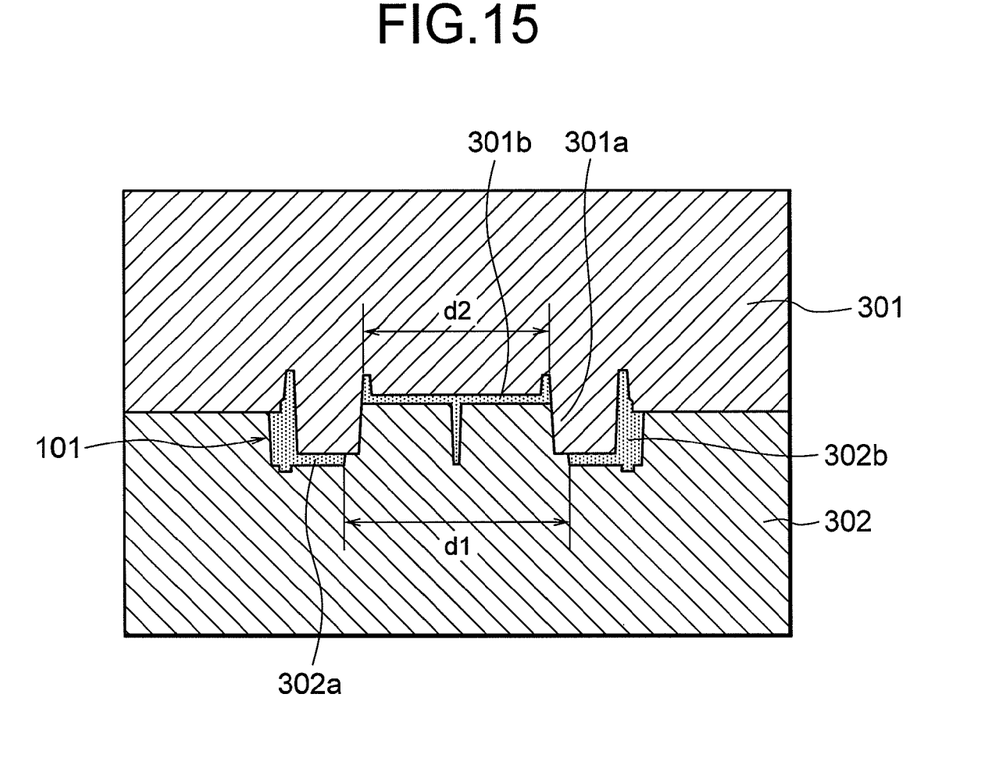
FIG. 15 is a sectional view illustrating an example of dies forming the laboratory dish main body.

FIG. 15 illustrates a cross section of an example of the dies for forming the laboratory dish body 101. Resin is filled in the cavity space between a first die 301 and a second die 302.

The internal diameter d2 of a cylindrical projection 301a surrounding a cavity 301b formed on the first die 301 for forming the internal cover 104, is smaller than the internal diameter d1 of a bottom 302a of a cavity 302b formed on the second die 302 for forming the laboratory dish body 101. For configuring the dies 301 and 302 as described above, the molded laboratory dish body 101 may be removed easily from the dies.

As shown in FIG. 12, the external cover 102 is fitted on the laboratory dish body 101 to cover the inside of the laboratory dish body 101 and the internal cover 104 in its entirety, thereby evaporation of culture medium may be restrained and contamination of the incubation chambers may be prevented.

The external cover 102 may be doughnut-shaped or annular-shaped in the same way as shown in FIG. 1. The operation and effects of such doughnut-shaped or annular-shaped external cover 102 are the same as those described on the first embodiment, so the descriptions thereon are omitted herein.
(Method of Use)

Method of using the laboratory dish of the fourth embodiments will be described below:

Liquids such as culture medium are poured into four incubation chambers through doughnut- or annular-shaped space formed between the inner diameter of the laboratory dish body 101 and the peripheral edge portion 104b of the internal cover 104, shown in FIG. 13.

Referring to FIG. 12, liquid surface at the doughnut-shaped space portion between the inner diameter of the laboratory dish body 101 and peripheral edge portion 104b of the internal cover 104, is opened and curvatured, while the liquid surface at the central portion is closed by the internal cover 104, so the liquid surface at the central area follows the flat portion 104a of the internal cover 104 to be flat. As a result, phase difference observation may be made with no problem even in the neighborhood of the partitioning wall 103a of the partitioning member 103 at the central area of the laboratory dish body 101.

It is preferable that the surface of each partitioning wall 103a of the partitioning member 103 is in parallel with the center axis I of the partitioning member 103.

In case where the combination of the partitioning member 103 and the internal cover 104 is integrally formed by injection molding, it becomes necessary to have a proper draft angle. For this purpose, each partitioning wall 103a of the partitioning member 103 is so inclined to subtend angle θ with respect to the center axis I of the partitioning member 103, as shown in FIG. 12, so that thickness of the partitioning member 103 may be smaller toward the lower end thereof from the upper end portion joined to the inner cover 104. It is preferable that the draft angle θ is made less than a predetermined one as described below.

Figure 16:
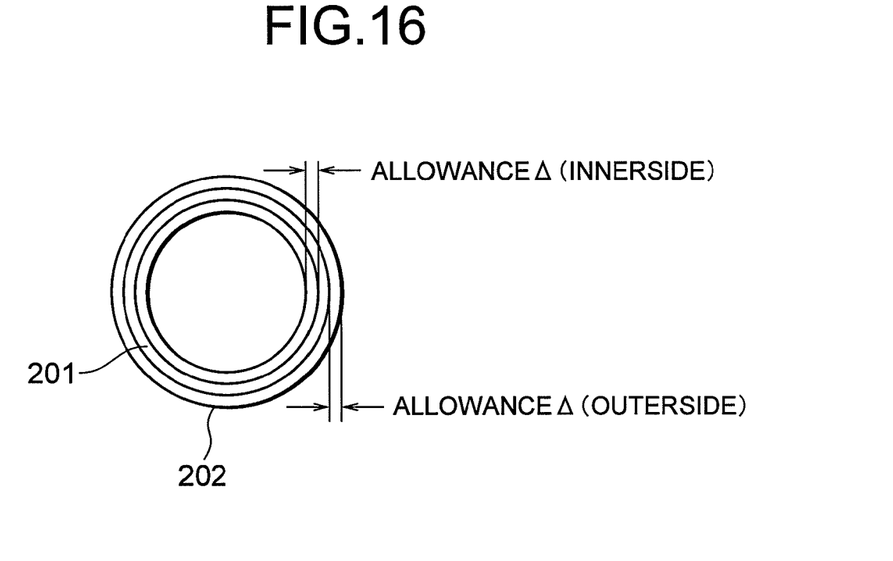
FIG. 16 is a view showing a positional relationship between a phase plate and a phase ring-shaped or annular-shaped stop at a pupil plane of an objective lens of a phase difference microscope.

FIG. 16 is a view showing a relationship between a ring-shaped phase stop and phase plate at the pupil plane of the objective lens of a phase difference microscope.

As shown in FIG. 16, according to a phase difference observation, illumination light is made to be annular-shaped through a ring-shaped phase stop 201 and illuminate a specimen. Direct light advancing straight through the inside of the specimen passes through the ring-shaped phase plate 202 in the objective lens located in the conjugate position with the ring-shaped phase stop 201, thereby the light being reduced and further phase-shifted by a ¼ wave length. This direct light and light diffracted through the specimen cause interference so that phase difference of the specimen (that is, difference in refractive indices) is converted to light intensity (or contrast), thus transparent specimen being visualized.

Generally, a phase difference microscope is so designed that all direct light may pass through the phase plate 202 in the objective lens. In a case where there is any leaked direct light from the ring-shaped phase plate 202 due to any reasons, such leaked light does not contribute to forming a phase-difference image, but moreover becomes stray light that is extremely larger in strength than the diffracted light since no reduction of the leaked light is caused. Such stray light deteriorates contrast of the phase difference image.

The phase plate 202 is so shaped to be conjugate optically with the ring-shaped phase stop 201, and generally the width of the phase plate is so designed to have larger allowance (Δ) than that of the phase ring stop 201 (refer to FIG. 16). This is a contrivance for preventing direct light from leaking from the phase plate 202, even when concentricity between the phase ring stop 201 and the phase plate 202 being losed due to errors and the like.

The surface of the partitioning member 103 reflects a part of illumination light at the interface between that surface and the culture medium. Assuming that the surface of the partitioning member 103 subtends an angle θ with respect to the center axis I of the partitioning member 103, the reflected illumination light has an angle of deviation 2θ, that is, twice as mush as the angle θ.

At this time, if the angle of deviation is so small to be within the allowance Δ (converted angle), direct light causes no leakage and the contrast would not be deteriorated. The angle θ between the center axis I and the surface of each partitioning wall 103a of the partitioning member 103, satisfies preferably the following conditional expression:

$$\theta < \Delta/(n \times 2)$$

where Δ is an angle converted from the allowance of the phase plate 202 with respect to the ring-shaped phase stop 201; θ denotes an angle between the surface of each wall of the partitioning member 103 and the center axis I; and n is refractive index of the culture medium. The angle θ is preferably less than 0.5 degree.

Of course, it is preferable that the surface of the flat portion 104a of the internal cover 104 or of the flat portion of the external cover 102 is optically smooth. It is also preferable that the vertical surfaces of the walls 103a of the partitioning member 103 are optically smooth. A rough surface such as a so-called mat surface scatters the illumination light, and direct light leaks from the phase plate in the same manner as described in the previous embodiment. This would cause a phenomenon in which contrast of the phase difference image is deteriorated in case where a portion of the specimen close to the vertical surface is observed.

The laboratory dish body 101 is formed with concaved portions 100a to be engaged with projections 20a (not shown) formed on the exterior cover 102. These projection 20a and the concaved portion 100a have the same functions and effects as those of the third embodiment shown in FIG. 10.

The present invention may provide a laboratory dish that is partitioned into a plurality of chambers for incubating the cells, which dish can restrain the meniscus effect caused by the partitioning member and enables liquids to be poured and replaced easily.

The invention claimed is:

1. An incubation container, containing cultured cells, for observation through a microscope, comprising:
   a bottom and a sidewall; a partitioning member water-tightly partitioning an interior of said incubation container into a plurality of incubation chambers by perpendicular walls and water-tightly fitting to or formed integrally with a portion of the bottom of said incubation container, thereby capable of retaining in separation a liquid inputted in each of said incubation chambers from liquids in other incubation chambers; and
   a cover member covering an upper portion of each of said incubation chambers partitioned by said partitioning member and water-tightly fitted to or formed integrally with said partitioning member, the cover member having an under surface located at a level lower than the top of the sidewall and having an upper surface surrounded by a peripheral wall,
   wherein a whole or part of said cover member is formed of a transparent member, and
   the upper portion of each of said incubation chambers is partly formed with an opening that is not covered by the cover member, via which to input the liquid in each of said incubation chambers.

2. The incubation container according to claim 1, wherein said cover member has a flat portion providing said under surface and a cylindrical edge portion providing said peripheral wall at an outside diametrical portion thereof and is positioned, with said flat portion being directed downward, concentrically with said incubation container in the interior of said incubation container,
   the outside diametrical portion of said cover member is formed smaller than an inside diametrical portion of said sidewall of said incubation container,
   said flat portion and said edge portion of said cover member are in contact with said partitioning member,
   a contact portion therebetween has the water-tightness, and said opening is formed between the inside diametrical portion of said sidewall of said incubation container and the outside diametrical portion of said cover member, whereby
   the liquids are poured via said opening into said incubation chambers and can fill up between said flat portion of said cover member and the bottom portion of said incubation container.

3. An incubation container, containing cultured cells, for observation through a microscope according to claim 1, further comprising a doughnut-shaped attachable/detachable member covering said opening, wherein said opening is formed between an inside diametrical portion of said sidewall of said incubation container and an outside diametrical portion of said cover member.

4. The incubation container according to claim 2, further comprising a doughnut-shaped attachable/detachable member covering said opening between the inside diametrical portion of said sidewall of said incubation container and the outside diametrical portion of said cover member.

5. An incubation container, containing cultured cells, for observation through a microscope, comprising:
   a container body for containing said cultured cells, the container body, having formed at a bottom thereof, an aperture;
   a first cover member that closes said aperture; a partitioning member partitioning an interior of said container body into a plurality of incubation chambers by perpendicular walls and tightly fitting to said cover member, thereby capable of retaining in separation liquid inputted in one of said incubation chambers from liquids in the other incubation chambers;
   a second cover member covering an upper portion of the incubation chambers partitioned by said partitioning member;
   said container body, said partitioning member and said second cover member being formed integrally; and
   said second cover member being so sized that an area of the second cover member projected on the bottom of the said container body is smaller than that of said aperture.

6. The incubation container according to claim 5, wherein said first cover member is bonded to an outer surface of the bottom portion of said container body and an lower end surface of said partitioning member.

7. The incubation container according to claim 5, wherein said first cover member comprises a cover made from a glass.

8. The incubation container according to claim 5, wherein said aperture and said second cover member are circular, and satisfying the following condition:

$$d2 < d1$$

where $d1$ is a diameter of said aperture; and $d2$ is a diameter of the second cover member.

9. The incubation container, containing cultured cells according to claim 5,
   wherein a surface of a wall of said partitioning member is inclined with respect to a center axis of the partitioning member.

10. The incubation container according to claim 9,
    wherein said surface of the wall of said partitioning member is inclined at an angle with respect to the center axis of the partitioning member that is so determined to satisfy the following conditional expression;

$$\theta < \Delta/(n \times 2)$$

where $\Delta$ is an angle converted from an allowance of a phase plate with respect to a ring-shaped phase stop; $\theta$ denotes an angle between the surface of each wall of the partitioning member and the center axis I thereof; and n is refractive index of the culture medium.

11. The incubation container according to claim 5, wherein the wall surface of said partitioning member and the wall surface of said second cover member are so formed to be optically smooth.

12. The incubation container according to claim 5, further comprising:
    a third cover member that covers removably an inner diameter portion of said container body.

13. The incubation container according to claim 12,
    wherein said third cover member covers a space formed between an inner diameter portion of said container and an outer diameter portion of said second cover member.

14. The incubation container according to claim 5, wherein the wall of said partitioning member and said first cover member are water-tight.

\* \* \* \* \*